United States Patent
Helmfridsson et al.

(10) Patent No.: US 6,602,237 B2
(45) Date of Patent: Aug. 5, 2003

(54) SANITARY NAPKIN WITH SEPARATE PROTECTIVE LAYERS ON ADHESIVE REGIONS

(75) Inventors: Bror-Inge Helmfridsson, Partille (SE); Hakan Persson, Gothenburg (SE); Solgun Drevik, Molnlycke (SE); Frantisek Solar, Gemerska Horka (SK)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 10/081,189

(22) Filed: Feb. 25, 2002

(65) Prior Publication Data

US 2002/0082579 A1 Jun. 27, 2002

Related U.S. Application Data

(62) Division of application No. 09/833,631, filed on Apr. 13, 2001.
(60) Provisional application No. 60/200,357, filed on Apr. 28, 2000.

(30) Foreign Application Priority Data

Apr. 13, 2000 (SE) ................................................ 0001379
Jun. 30, 2000 (SE) ................................................ 0002475

(51) Int. Cl.$^7$ ................................................ A61F 13/15
(52) U.S. Cl. ............................ 604/385.04; 604/385.05; 604/390
(58) Field of Search ..................... 604/385.01–385.05, 604/386, 387, 389, 390

(56) References Cited

U.S. PATENT DOCUMENTS

| | | | |
|---|---|---|---|
| 5,429,630 A | * | 7/1995 | Beal et al. ............. 604/385.04 |
| 5,453,143 A | | 9/1995 | Menard |
| 5,713,886 A | * | 2/1998 | Sturino .................. 604/385.04 |

FOREIGN PATENT DOCUMENTS

| | | |
|---|---|---|
| EP | 0 280 998 | 9/1988 |
| EP | 0 749 742 | 12/1996 |
| WO | 98 20823 | 5/1998 |

* cited by examiner

Primary Examiner—Weilun Lo
Assistant Examiner—C L Anderson
(74) Attorney, Agent, or Firm—Young & Thompson

(57) ABSTRACT

An absorbent product includes an absorbent portion with an absorbent body between a liquid permeable sheet and a liquid impermeable sheet, and flexible flaps projecting from tapering longitudinal edges of the absorbent portion. A first removable protective layer covers substantially the entire absorbent portion and second and third removable protective layers each cover substantially all of a respective one of the flexible flaps. Each of the second and third protective layers is directly opposite the first protective layer along substantially an entire length of a first line along the respective longitudinal edge of the absorbent portion. The second and third protective layers are at least partially separated from the first protective layer by a cut line that follows the respective first line.

4 Claims, 2 Drawing Sheets

SANITARY NAPKIN WITH SEPARATE PROTECTIVE LAYERS ON ADHESIVE REGIONS

FIELD OF INVENTION

The present invention relates to a method of providing an absorbent article, such as a sanitary napkin, a panty liner or an incontinence protector for women, with protective layers that cover the adhesive regions of the article, said article including an absorbent body or pad which is sandwiched between a liquid-permeable outer sheet and a liquid-impermeable outer sheet and which is provided with a flexible flap that projects out from each longitudinal edge of the article along a part of each said longitudinal edge, wherein the flaps are intended to be folded around the edge of a panty or a pair of underpants and fastened to the outside thereof or to each other when the article is worn, and have adhesive regions on the outside of the liquid-impermeable outer sheet on at least one of the flaps and on that part of said outer sheet that extends over the absorbent body. The invention also relates to an absorbent article provided with protective layers.

BACKGROUND OF THE INVENTION

Sanitary napkins that include outwardly projecting, flexible wings or flaps, which most often consist in laterally extended portions of the outer sheet of the napkin and which are intended to be folded around the edges of a pair of panties and fastened to the outside of the panties after having fastened the napkin to the inside of the panties, have become very popular with the users of sanitary napkins. In order to enable such napkins to be fastened to panties, the napkins are provided with adhesive regions on the outer sheet that lies proximal to the panties, both on the flaps and on that part of the napkin which is fastened to the inside of the panties. In order to protect these adhesive regions from contaminants such as dust and similar substances, and to prevent the adhesive drying out and also to facilitate handling of the napkins, the adhesive regions are covered with protective layers that are removed when fitting the napkin into a pair of panties. These protective layers normally comprise so-called release paper, which consists of silicone-coated paper and which can be removed easily from the adhesive regions without impairing the adhesiveness of the adhesive.

So-called string panties, i.e. panties with which the rear part of the crotch portion of the napkin is very narrow, have become very popular in recent times, and sanitary napkins designed to fit into string panties have been produced. Because conventional sanitary napkins that include wings or flaps have been widely appreciated by the users of such napkins, it is desirable to include such flaps also on sanitary napkins that are intended for use with string panties.

In the manufacture of conventional flap-equipped sanitary napkins, the adhesive layers and protective layers are applied by cutting the respective flap-protecting layers and the layers for protecting that part of the napkin which includes the absorbent body from separate reels of protective layer material and then mounting these layers on the napkin. Prior to cutting these separate protective layers from the different reels of material, adhesive is applied to said layers in those patterns intended for the adhesive regions of the napkin.

This application process cannot be applied to flap-equipped sanitary napkins for string panties, because the flaps of such napkins must, of necessity, be relatively narrow and will be inclined to the longitudinal symmetry axis of the napkin. A rectangular strip of protective layer material that has a width corresponding to the width of the adhesive pattern on the flap will then extend outwardly of the inclined flap on opposite sides thereof.

The object of the present invention is to enable protective layers to be applied to flap-equipped sanitary napkins that are designed to be worn in string panties, in a simple and uncomplicated fashion with the aid of conventional equipment and in a manner such that the production rate of a production line for the production of such napkins will not be impaired by the application of said protective layers.

SUMMARY OF THE INVENTION

This object of the invention is achieved with a method of providing an absorbent article, such as a sanitary napkin, a panty liner or an incontinence protector for women, with protective layers that cover the adhesive regions of the article, said article including an absorbent body or pad which is sandwiched between a liquid-permeable outer sheet and a liquid-impermeable outer sheet or backing sheet and which includes a flexible flap that projects out from each longitudinal edge of the article along a part of each said longitudinal edge, wherein the flaps are intended to be folded around the edge of a panty and fastened to the outside of the panty when the article is worn and have adhesive regions on the outside of the liquid-impermeable outer sheet on at least one of the flaps and on that part of said outer sheet that extends over the absorbent body, said article being characterised in that a rectangular protective layer that has a width corresponding to the greatest width of the article and a length that corresponds to the length of the article is provided with two cuts which when the protective layer is applied to an article extend linearly between the points at which the flaps adjoin the longitudinal edges of said article; in that the cut protective layer is placed on the article so that the two cuts extend linearly between the points of connection of the flaps to the longitudinal edge of the article; and in that a contour corresponding to the outer contour of the article is cut from the rectangular protective layer. This method results in the application of a continuous and stable protective layer on each article, said layer being divided into separate respective layers for the flaps and for that part of the article which includes the absorbent body whilst cutting out the finished article at the same time. Thus, only one single protective layer is applied to the article when practicing the present invention.

The invention relates in particular to a method of providing absorbent articles in the form of sanitary napkins, panty liners or incontinence protectors for women continuously with protective layers that cover the adhesive regions of the article in the continuous manufacture of such absorbent articles; wherein each article includes an absorbent body that is enclosed between a liquid-permeable outer sheet and a liquid-impermeable outer sheet, and further includes a flexible flap that projects out from each longitudinal edge of the article along a part of each said longitudinal edge, wherein the flaps are intended to be folded around the edge of a panty or a pair of pants when used, and fastened to the outside of said panty or pants, and have adhesive regions on the outside of the liquid-impermeable outer sheet on at least one of the flaps and on that part of said outer sheet that extends over the absorbent body. The article is characterised in that a web of protective layer material that has a width which corresponds at least to the greatest width of the article seen at right angles to the machine direction is provided with a sequence of pairs of cuts which are so spaced apart that when the web of protective layer material is mounted on a web of article blanks the two cuts in each pair of mutually sequential pairs of cuts will lie linearly between the points at which the flaps connect with the longitudinal edges of each article; and is further characterised in that the thus cut web of protective layer material is placed on a web of article blanks so that the two cuts in each pair of mutually sequential pairs of cuts will extend linearly between the points at which the flaps connect with the longitudinal edges of each article; and in that individual article provided with protective layers are cut from the composite web of article blanks and the web of protective layer material. Because complete separation of the protective layers on the flaps from the protective layer on the part of the article that includes the absorbent body is not effected until final separation of individual articles from the composite web of material, the method enables protective layers that extend while inclined to the machine direction to be readily achieved with conventional equipment without impairing the production rate.

In one preferred embodiment of the invention, the web of protective layer material is coated with a sequence of patterns of adhesive regions that correspond to the patterns of adhesive with which each article shall be provided prior to cutting the web of protective layer material and placing said material on the web of article blanks. The web of protective layer material is placed on the web of article blanks subsequent to the row of absorbent bodies on this latter web having been enclosed between two webs of outer sheet material.

According to one variant, the web of protective layer material is applied to the web of liquid-impermeable outer sheet material prior to said web having been combined with the row of absorbent bodies.

In another variant, the cuts extend beyond the long edges of the article and have at each end a section that curves outwards in relation to the longitudinal axis of the article. The outwardly curved end-part of respective cuts may be terminated with inwardly curved sections that connect with the linear part of said sections at points which lie between the points at which the flaps connect with the longitudinal edges of each article, when the web of protective layer material is mounted on a web of article blanks. The resultant pieces cut from the web of protective layer material are removed prior to placing said web on the web of article blanks.

In the case of one preferred embodiment, the cuts are discontinuous, preferably so as not to reach the points at which the flaps connect with the longitudinal edges of the article.

The invention also relates to an absorbent article in the form of a sanitary napkin, a panty liner or an incontinence protector for women comprising an absorbent body which is enclosed between a liquid-permeable and a liquid-impermeable outer sheet and which includes a flexible flap that projects out from each longitudinal edge of the article and extends along a part of each said longitudinal edge, said flaps being intended to be folded around the edge of a string panty when the article is worn and fastened to the outside of said panty. The article has regions of adhesive on the outside of the liquid-impermeable outer sheet on the flaps and on that part of the outer sheet that extends over the absorbent body, wherein the absorbent body has a front part and a rear part and tapers rearwardly from a section of greatest width in the front part of the article to its rear end. The article is characterised in that it includes a first protective layer that is fastened to the adhesive regions of the part of the liquid-impermeable surface sheet that includes the absorbent body and that extends over the whole of this part and can be easily removed therefrom, and further includes two other protective layers each of which are fastened to one of the flaps and which extend over essentially the whole of this flap and can be easily removed therefrom, and wherein the edges of the second protective layers facing towards the absorbent body and the bordering edges of the first protective layer extend linearly between each of the points at which the flaps connect with the longitudinal edges of the article. Such an article has many advantages. For instance, it can be readily manufactured, has separate protective layers for flaps and that part of the article which includes the absorbent body, facilitates inward folding of the flaps, and can be easily handled and easily folded for packaging purposes.

In one advantageous variant, the flaps have no protective layer on their front and rear end-parts.

In one preferred variant, the protective layers removably fasten to the flaps are each connected to the first protective layer via at least one narrow bridge of material between adjacent edges of said protective layers. The bridges are preferably located in the ends of the edges of the protective layers removably fastened to the flaps and bordering on the longitudinal edges of the first protective layer. The bridges have a width of 1–10 mm, preferably 3–5 mm.

BRIEF DESCRIPTION OF THE DRAWINGS

The invention will now be described with reference to the accompanying drawings, in which.

DESCRIPTION OF EMBODIMENTS

Figure 1:
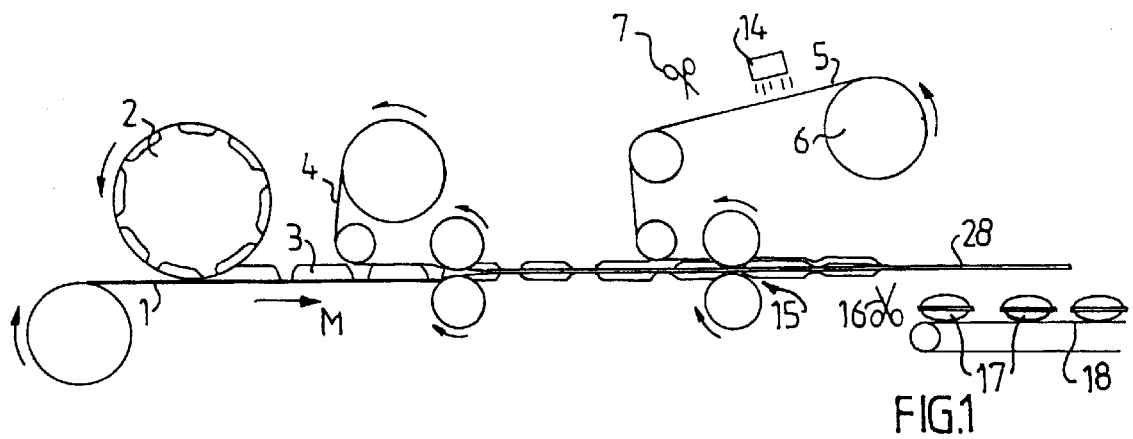
FIG. 1 illustrates schematically an arrangement for manufacturing a sanitary napkin in which there is used one embodiment of an inventive method of applying a protective layer to the napkin.

In the embodiment of the arrangement illustrated in FIG. 1, a web 1 of liquid-permeable outer sheet or surface sheet material is passed through the arrangement in a feed direction M in some suitable way, for instance with the aid of vacuum conveyors. A row or line of mutually spaced absorbent bodies 3 are placed on the web 1 in the machine direction with the aid of a transfer wheel 2, whereafter a web 4 of liquid-impermeable outer sheet or backing material is placed on top of the row of absorbent bodies. The two webs 1 and 4 are then joined together in areas that lie outwardly of the absorbent bodies 3, e.g. by ultrasound welding, heat welding or gluing. The components of the arrangement shown in FIG. 1 described hitherto and the use of such components is well known to the person skilled in this art and need not be described in more detail.

Figure 2:
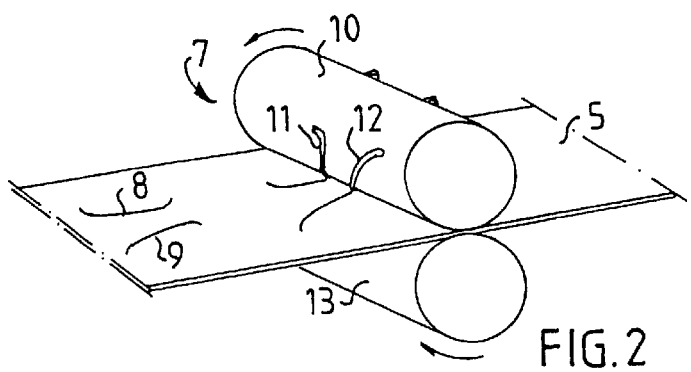
FIG. 2 illustrates schematically a device for making cuts in a web of protective layer material.

According to the invention, a web 5 of protective layer material is taken from a storage reel 6 and passed through a cutter 7 that functions to make mutually separate cuts 8, 9 in the web, said cuts diverging relative to one another in the direction of web movement. As shown schematically in FIG. 2, the cutter 7 may comprise a cutting roll 10 that includes one or more pairs of obliquely extending pairs of cutting edges or blades 11, 12, and a counterpressure or anvil roll 13. Prior to passing the cutter 7, the web 5 passes a glue applicator 14, shown schematically in FIG. 1. The glue applicator 14 will suitably include a number of glue nozzles that apply strings of glue to the web 5 in a given glue pattern. The web 5 is then placed on the composite web consisting of the webs 1 and 4 and the intermediate row of absorbent bodies 3, and the webs are passed through a pair of rolls 15 which ensure that the glue strings are fastened effectively to the web 4. Finally, individual sanitary napkins 17 are cut from the composite web comprising the webs 1, 4, 5 and the row of absorbent bodies 3, with the aid of a further cutter 16.

Figure 3:
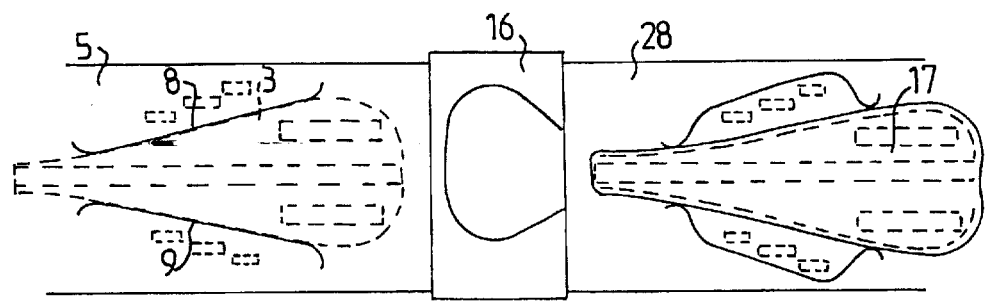
FIG. 3 illustrates the arrangement of FIG. 1 in a final stage of manufacture, schematically and in plan view.

FIG. 3 illustrates schematically the final stage in the manufacture of sanitary napkins in the arrangement according to FIG. 1. As will be seen from the Figure, the pairs of cutting lines 8, 9 in the web 5 extend along mutually opposite edge parts of the absorbent bodies 3 with the exception of the ends of said lines, which are curved outwardly. When the web 5 passes the cutter 16, which may have the form of a cutting roll that includes one or more cutting knives or blades corresponding to the contour of the napkins to be cut from the web, individual napkins 17 are cut from the web 5 and fall down onto an appropriate conveyor 18, for transportation to a napkin folding and packaging station.

In the case of the described embodiment, the absorbent bodies 3 move with their front edges leading in the direction of movement of the web 1. As will be understood, if the absorbent bodies are instead delivered to the web 1 with their rear edges leading, the cuts 8, 9 in the web 5 must, of course, be adapted accordingly and formed so as to converge relative to one another in the direction of web movement.

Figure 4:
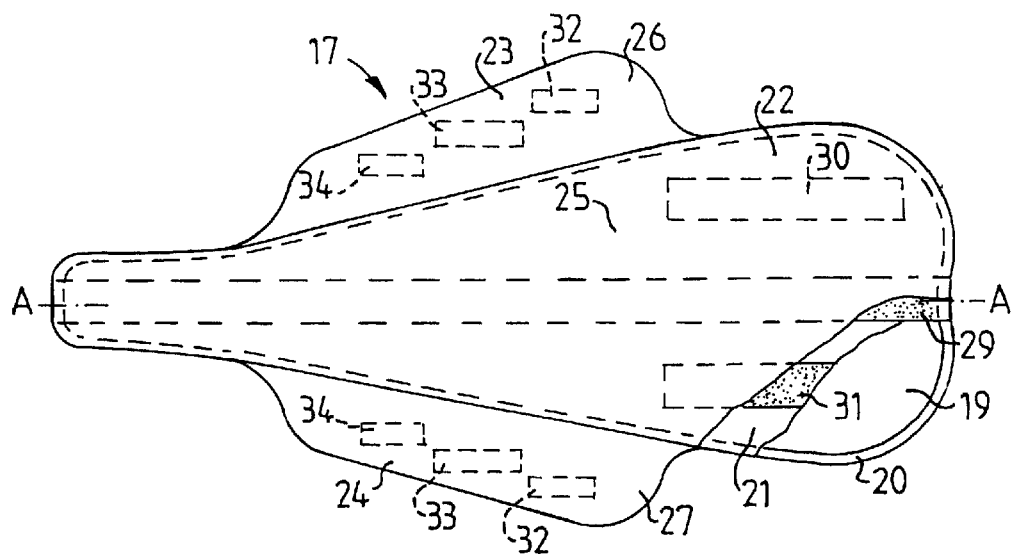
FIG. 4 is a schematic, partially cut-away plan view of a sanitary napkin manufactured by means of the arrangement of FIG. 1.

FIG. 4 illustrates a sanitary napkin 17 manufactured in the aforedescribed arrangement. This napkin 17 includes an absorbent body 19 which is enclosed between a liquid-permeable outer sheet or surface sheet 20 and a liquid-impermeable outer sheet or backing sheet 21. The outer sheets 20, 21 are joined together at parts which lie outwardly of the absorbent body. The napkin 17 is intended to be worn in a string panty, and the absorbent body 19 therefore tapers rearwardly from the widest part of a front napkin part 22 to the rear end of the napkin. The outer sheets 20, 21 form outwardly projecting flaps 23, 24 or wings, which are intended to be folded around the edges of a string panty and fastened to the outside thereof. The flaps 23, 24 extend longitudinally outside the edges of the absorbent body 19 with substantially the same width, and the longitudinal edges of the flaps therewith converge towards each other in the rear direction. In the case of the illustrated embodiment, the length of the flaps corresponds to about half the length of the napkin, and the flaps are spaced slightly further from the forward end of the napkin than from its rearward end.

The illustrated napkin has a length of 140–260 mm. The absorbent body has a greatest width of 70 mm and a smallest width at its rear end of about 10 mm. The flaps extend beyond the edges of the absorbent body through a distance of about 25–30 mm, with the greatest distance in the front parts of the flaps. The front edges of the flaps are located about 60 mm from the front edge of the napkin, and their rear edges are located about 50 mm from the rear end of said napkin. It will be understood that the aforesaid measurements are merely intended to give a qualitative understanding of a suitable design of a sanitary napkin for string panties and in no way limit the scope of the invention.

The liquid-permeable outer sheet 20 is comprised of a soft, skin-friendly material. Examples of suitable materials in this respect are different types of nonwoven fibre material. Other materials that can be used are perforated plastic film, plastic nets or knitted, crocheted or woven textiles, and combinations and laminations of said types of material. The plastic material may be a thermoplastic, e.g. polyethylene (PE). The nonwoven material may be comprised of natural fibres, such as cellulose or cotton, although it may alternatively consist of synthetic fibres, such as polyethylene PE, polypropylene (PP), polyurethane (PU), a polyester, nylon or regenerated cellulose, or a mixture of different fibres. All materials that are used to produce liquid-permeable outer sheets in absorbent articles can be used for the liquid-permeable outer sheet 20, it being understood that the aforesaid materials have been given solely by way of example.

The liquid-impermeable outer sheet 21 is comprised of a flexible material, preferably a thin plastic film of PE, PP or a polyester, although it may alternatively comprise a liquid-permeable material, such as nonwoven, laminated with a liquid-impermeable material. All materials that are used to provide liquid-imperious outer sheets for absorbent articles can be used. The outer sheet 21 may conveniently be air permeable.

The absorbent body 19 is preferably comprised of cellulose fibres, although other natural materials, such as cotton wool fibres or peat pulp may be used. Alternatively, the absorbent body may be comprised of absorbent synthetic fibres or of a mixture of natural and synthetic fibres. The absorbent body may also include a superabsorbent, i.e. a polymer that is able to absorb liquid in an amount corresponding to several times its own weight. The absorbent body may also include shape stabilising means and liquid dispersing means, and also a binder for holding together short fibres and particles to form a coherent unit. The absorbent body may also be comprised of more than one layer of absorbent material.

The entire sanitary napkin 17 is covered with three protective layers 25, 26, 27, of which the protective layer 25 covers the whole of the napkin with the exception of the flaps 23, 24, and each of the layers 26, 27 covers a respective flap. Because the outwardly curved end-parts of the cut lines 8, 9 extend beyond the contours of the finished napkin 17, the end-parts thereof will be crossed when contour-cutting the napkin in the cutter 16, as illustrated schematically in FIG. 3. When contour-cutting the napkin, the coherent, cut web 5 of protective layer material is thus divided into four parts for each napkin cut from the web, these being a first part 25 which covers the absorbent body 19, a second and a third part 26, 27 which each cover a respective flap 23, 24, and a fourth part 28 which consists of parts of the web 5 that lie outside the contours of the napkin. The mutually sequential parts 28 of the web 5 that remain subsequent to passage of the cutter 16 hang together and can be easily recovered together with remaining coherent parts of the webs 1 and 4 that also remain after contour-cutting of the napkin in the device 16.

In the case of the illustrated embodiment, the pattern of glue strings applied to the web 5 and thereafter pressed firmly onto the liquid-impermeable outer sheet 4 in the arrangement shown in FIG. 1 comprises three glue strings 29, 30, 31 disposed on the part of the outer sheet 21 that covers the absorbent body 19 and three glue strings 32, 33, 34 on each flap 23, 24. The glue string 29 extends along the longitudinal symmetry line A—A of the napkin 17 along the full length of said napkin, whereas the glue strings 30, 31 extend solely in the front part 22 of the napkin, on respective sides of the glue string 29. The glue strings 32, 33, 34 on the flaps 23, 24 are offset relative to each other in both the longitudinal and the transverse direction of the napkin. All glue strings in the illustrated flat state of the napkin extend parallel with the longitudinal symmetry axis of the napkin immediately after manufacture. The glue applicator unit 14 may therefore have a simple construction, e.g. may comprise a row or line of glue nozzles.

The protective layers 25, 26, 27 may conveniently comprise silicone-coated paper, so-called release paper, although other material that has poor adhesion to the glue used may be employed, e.g. foam material that has a surface which presents a small contact surface area. A silicone-treated protective paper normally used in this respect is ESP 48 marketed by Lohjan Paperi OY, Finland.

The glue used is suitably a pressure-sensitive hotmelt glue, such as Ecomelt H145 from Collano, Switzerland, although other commercially available pressure-sensitive adhesives can be used, including adhesives that are pressure-sensitive in a cold state, such as acrylate glue, these adhesives normally being combined with a stickiness-enhancing agent, such as terpense resin, or hotmelt glue such as styrene or butadiene co-polymers.

When placing the sanitary napkin 17 in a string panty, the protective layer 25 on that part of the outer sheet 21 which includes the absorbent body is removed and the napkin then fastened in its intended position. Because the protective layer 25 covers all glue strings 29, 30, 31 on this part of the napkin, the glue strings can be exposed with a single, simple hand movement, which is appreciated by the users. Furthermore, the protective layers on respective flaps 26, 27 are separate from the protective layer 25, meaning that there is no risk of the flaps sticking unintentionally to the user or to any part of her clothing when fitting the napkin inside the panty. The napkin can be fitted more easily into the panty, when the flaps are folded away against the liquid-permeable outer sheet 20 of the napkin. Because the protective layers on respective flaps lie edge-to-edge with the longitudinal edges of the protective flap 25, there is formed a natural flap folding line that facilitates folding the flaps out of the way. Furthermore, the protective layers 26, 27 stiffen the highly flexible flaps 23, 24 so that the flaps can be handled more easily. Folding away of the flaps is carried out as a stage in the napkin folding procedure undertaken for packaging purposes. Subsequent to placing the napkin in position in the panty, the protective layers 26, 27 are removed from the flaps 23, 24 and the flaps folded around the edges of the panty and fastened to the underside thereof.

Figure 5:
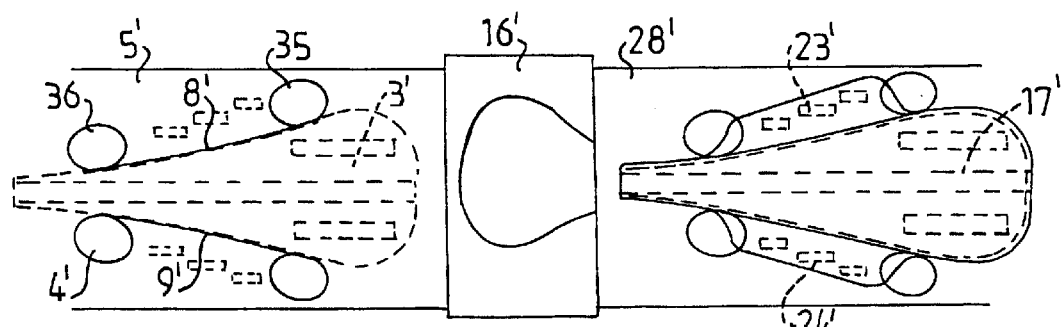
FIG. 5 illustrates schematically a second embodiment of the invention in a view similar to that of FIG. 3.

FIG. 5 is a view similar to that of FIG. 3, showing a second embodiment of the invention. The only difference between the embodiment illustrated in FIGS. 1–4 and the embodiment illustrated in FIG. 5 is that the cutter 7' of the FIG. 5 embodiment is adapted to cut parts from the web 5' at the end-parts 35, 36 of the cuts 8', 9'. The arrangement is constructed in precisely the same manner as the arrangement shown in FIGS. 1–3 in other respects and all other components are identical therewith, which enables FIG. 1 to be used to describe the second embodiment. Those components in FIG. 5 that find correspondence in the components shown in FIG. 3 have consequently been identified with the same reference signs to which a prime has been added. As will be seen from FIG. 5, the outwardly curved end-parts of the cut lines 8', 9' have been supplemented with inwardly curved end-parts 35, 36 that extend back towards the main parts of said cut lines and up to said main parts so that the areas defined by the end-parts 35, 36 of the lines 8', 9' will be cut away from the web 5' as the web passes the cutter 7'. This will be evident from FIG. 5, where the web 4' appears in the holes formed in the web 5' when cutting away said parts. With respect to the napkin 17' cut from the web after passage of the cutter 16', this means that the flaps will lack a protective layer within regions close to the points at which the flaps join the longitudinal edges of the napkin 17'. This is beneficial by virtue of the fact that there is otherwise a risk of these regions or areas standing up from the remainder of the protective layer on the flap subsequent to folding the flap in against the liquid-permeable outer sheet.

Figure 6:
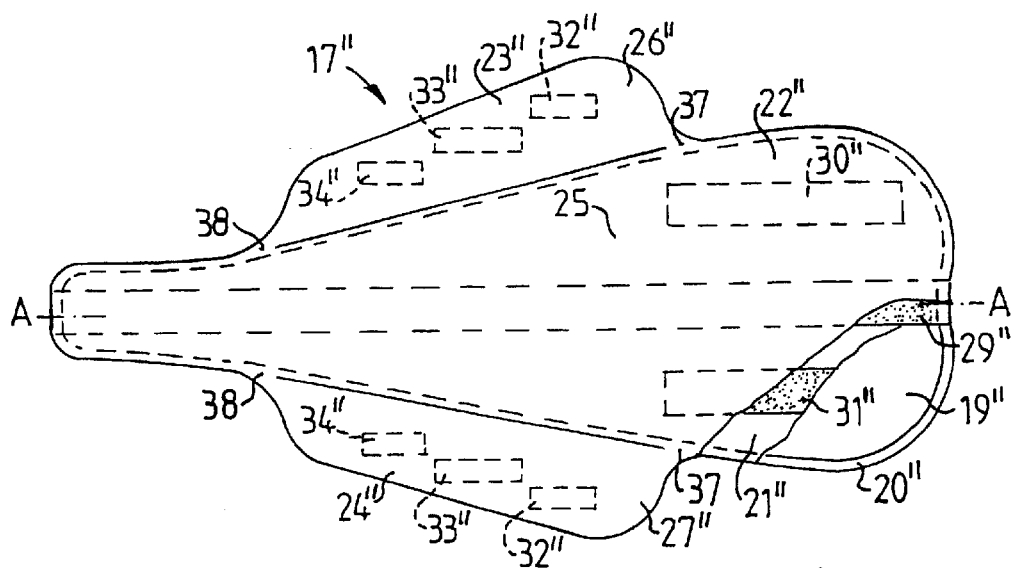
FIG. 6 is a view similar to that of FIG. 4 and shows a sanitary napkin according to a third embodiment of the invention.

In another preferred method of avoiding upstanding edge parts of the flap protective layers after folding said flaps in towards the liquid-permeable surface sheet, the cuts 8 and 9 are made discontinuously, preferably so that said cuts terminate short of the points at which the flaps join the longitudinal edges of the article. This will leave bridges that mutually connect the different protective layers. FIG. 6 is a view similar to that of FIG. 4 and illustrates a third preferred embodiment of an inventive sanitary napkin 17". The sanitary napkin 17" is, in principle, constructed similarly to the sanitary napkins 17 and 17' and differs from the embodiments described with reference to FIGS. 1–5 solely by virtue of the cutter being adapted to produce discontinuous cuts. In other respects, the manufacturing arrangement is constructed in precisely the same way as the arrangement according to FIGS. 1–3 and all other components are mutually the same, therewith enabling FIG. 1 to be used to describe the third embodiment. Those components in FIG. 6 that find correspondence with components in FIG. 4 have therefore been identified with the same reference signs to which a double prime has been added. In the case of the sanitary napkin 17" illustrated in FIG. 6, the edges bordering between the protective layers 25" and respective protective layers 26", 27" on the flaps 23", 24" are interconnected by bridges 37, 38 situated at the ends of respective edges of the flap protective layers. When folding-in the flaps, these bridges will prevent parts of the flap protective layers from lifting up from the flaps. It is preferred to place the bridges 37, 38 at the ends of the protective layer of the flaps facing towards the edges of the protective layer 25", as this can be readily achieved simply by causing the cutter to make shorter cuts. However, it is, of course, possible to construct the cutter to form discontinuous cuts in some other way, e.g. by leaving bridges of material in the centre portions of adjacent edges. It is also conceivable to provide a bridge solely in one end of the edge on the protective layers of respective flaps, although this is not preferred.

The bridges 37, 38 will preferably be so narrow that the force required to draw the bridges apart will be smaller than the force at which the protective layers 26", 27" adhere to the flaps 23", 24", so as to enable the protective layer 25" to be removed without being accompanied by any of the layers 26", 27" on the flaps. The bridges 37, 38 have a width of 1–10 mm, preferably 3–5 mm and more preferably about 4 mm.

The aforedescribed method of applying protective layers to absorbent articles has many advantages over known methods, in which several webs of protective layer material are used to protect different glue coatings on the article. Firstly, the actual application of protective layers is facilitated by the fact that only one single continuous web of protective layer material need be applied to a web of article blanks. This means that even flaps that are narrow and that are inclined to the machine direction can be readily provided with protective layers, and that protective layers which extend over the whole of that part of the article which includes the absorbent body can be formed regardless of glue pattern and regardless of the shape of the absorbent body. The inventive method can also be readily applied procedurally. Furthermore, the inner edges of the flap protective layers lie edge-to-edge with the central protective layer, therewith providing natural flap folding lines. These natural folding lines facilitate folding and packaging of the article. The protective layers on respective flaps also stiffen the flexible material of the flaps, which facilitates handling of the flaps up to the point at which the flaps are fastened to the outside of a panty.

Although the method is particularly useful for providing protective layers on sanitary napkins or similar articles that shall be fastened to string panties, it can, of course, also be applied to provide protective layers on flap-equipped sanitary napkins that shall be fastened to conventional panties or underpants.

It will be understood that the described embodiments can be modified within the scope of the invention. For instance, the web of protective layer material can be placed on the web of liquid-impermeable outer sheet material prior to combining said web with the row of absorbent bodies. The absorbent bodies can be mounted in some way other than with the aid of transfer wheels. The absorbent bodies may also have a shape different to that illustrated and the glue patterns may also be different. It is also conceivable to include in the illustrated arrangement means for mounting elastic or means for profiling the absorbent body. The flaps may also be designed to mutually overlap when folded in against the outside of a panty, and to be adapted to be fastened to each other instead of to the panty, in which case only one of the flaps need be provided with adhesive. The glue string extending along the symmetry line of the napkin need not extend over the full length of the napkin, but may terminate short of the front edge thereof. The invention is therefore limited solely by the contents of the accompanying claims.

What is claimed:

1. An absorbent product, comprising:

an absorbent portion with an absorbent body between a liquid permeable sheet and a liquid impermeable sheet, said absorbent portion having a front part and a rear part and tapering longitudinal edges that taper from a section of greatest width at said front part to a section of narrower width at said rear part;

flexible flaps projecting from said tapering longitudinal edges of said absorbent portion, each of said flexible flaps having a periphery that joins a periphery of said absorbent portion at forward point and rearward point, said forward and rearward points being joined by a first line that corresponds to a respective one of said tapering longitudinal edges;

first adhesive regions on said liquid impermeable sheet over said absorbent portion;

second adhesive regions on said flexible flaps;

a first removable protective layer covering substantially all of said absorbent portion and fastening to said first adhesive regions; and second and third removable protective layers, each covering substantially all of a respective one of said flexible flaps and fastening to said second adhesive regions thereon;

each of said second and third removable protective layers being directly opposite said first removable protective layer along substantially an entire length of a respective said first line and being at least partially separated from said first removable protective layer by a cut line that follows substantially all the respective said first line, wherein said cut line has a gap at a bridge that joins said first removable protective layer to a respective one of said second and third removable protective layers.

2. The product of claim 1, wherein said bridge is adjacent to a respective one of said forward and rearward points.

3. The product of claim 1, wherein said bridge has a width of 1 to 10 mm.

4. The product of claim 1, wherein said bridge has a width of 3 to 5 mm.

* * * * *